US008067247B2

(12) United States Patent
Belin et al.

(10) Patent No.: US 8,067,247 B2
(45) Date of Patent: Nov. 29, 2011

(54) USE OF ANTI-CD100 ANTIBODIES FOR THE TREATMENT OF INFLAMMATORY DISORDERS AFFECTING THE CENTRAL OR PERIPHERAL NERVOUS SYSTEM

(75) Inventors: Marie-Françoise Belin, Lyons (FR); Pascale Giraudon, Lyons (FR); Laurence Boumsell, Paris (FR); Armand Bensussan, Paris (FR)

(73) Assignee: Institut National de la Sante Et de la Recherche Medicale (INSERM), Paris (FR)

( * ) Notice: Subject to any disclaimer, the term of this patent is extended or adjusted under 35 U.S.C. 154(b) by 312 days.

(21) Appl. No.: 10/544,031

(22) PCT Filed: Feb. 2, 2004

(86) PCT No.: PCT/EP2004/001743
§ 371 (c)(1),
(2), (4) Date: Jun. 14, 2006

(87) PCT Pub. No.: WO2004/067034
PCT Pub. Date: Aug. 12, 2004

(65) Prior Publication Data
US 2006/0233793 A1    Oct. 19, 2006

(30) Foreign Application Priority Data
Jan. 31, 2003  (EP) .................................... 03290247

(51) Int. Cl.
| | | |
|---|---|---|
| G01N 33/53 | (2006.01) | |
| A61K 39/395 | (2006.01) | |
| A61K 39/00 | (2006.01) | |
| C07K 16/00 | (2006.01) | |
| C12P 21/08 | (2006.01) | |

(52) U.S. Cl. ........ 436/547; 436/548; 436/543; 436/544; 436/545; 436/546; 424/130.1; 424/141.1; 424/142.1; 530/388.1

(58) Field of Classification Search ........................ None
See application file for complete search history.

(56) References Cited

U.S. PATENT DOCUMENTS

| | | | | |
|---|---|---|---|---|
| 6,576,754 B2 * | 6/2003 | Hall et al. | ..................... | 536/23.5 |
| 6,635,742 B1 * | 10/2003 | Boyle et al. | ................ | 530/387.1 |
| 2003/0158402 A1 | 8/2003 | Hall et al. | | |

FOREIGN PATENT DOCUMENTS

| | | |
|---|---|---|
| WO | WO-93/14125 | 7/1993 |
| WO | WO 93/14125 A1 | 7/1993 |
| WO | WO 95/07706 A1 | 3/1995 |
| WO | WO 97/17368 A1 | 5/1997 |

OTHER PUBLICATIONS

't Hart et al. Curr. Opin. Neurol. 2003. 16: 375-383.*
Burgess et al. J of Cell Bio. 111:2129-2138, 1990.*
Pawson et al. 2003, Science 300:445-452.*
Campbell et al. Neuron. 2006, 52:77-92.*
Kumanogoh, et al, "Class IV semaphoring Sema4A enhances T-cell activation and interacts with Tim-2" Oct. 10, 2002, pp. 629-933, vol. 419, No. 6907, Nature, London.
Herold et al, "Activation signals are delivered through two distinct epitopes of CD100, a unique 150 kDa human lymphocyte surface structure previously defined by BB18 Ab", 1995, pp. 1-8, vol. 7, No. 1, International Immunology.
Goldsby, et al, "Kuby Immunology, 4th ed.", 2000, p. 502 & 504.
Levin, et al, "Molecular mimicry to neurons results in neurological disease", 2002, pages Abstract No. 415.3, vol. 2002, 32nd Annual meeting of the society for neuroscience, Orlando, FL.
Wang, et al, "Functional soluble CD100/Sema4D released from activated lymphocytes: Possible role in normal and pathologic immune responses", Jun. 1, 2001, pp. 3498-3504, vol. 97, No. 11, Blood, W.B. Saunders Company, Orlando, FL.
Delaire, et al, "Inhibition of immune cell migration by soluble CD100 and H-Sema Iiisemaphorins", Jun. 20, 2000, p. 103, vol. 55, No. SUPPL 1, Tissue Antigens, Munksgaard, Copenhagen, DK.
Kumanogoh, et al, "The CD100-CD72 interaction: a novel mechanism of immune regulation", Dec. 1, 2001, pp. 670-676, vol. 22, No. 12, Trends in Immunology, Elsevier, Cambridge, GB.
Kumanogoh, et al "Requirement for the lymphocyte semaphoring, CD100, in the induction of antigen-specific T cells and the maturation of dendritic cells", Aug. 1, 2002, pp. 1175-1181, vol. 169, No. 3, Journal of Immunology.
Giraudon, et al "Semaphorin CD100 from activated T lymphocytes induces process extension collapse in oligodendrocytes and death of immature neural cells", Jan. 15, 2004, pp. 1246-1255, vol. 172, No. 2, Journal of Immunology.
Delaire, S., et al., "Inhibition of Immune Cell Migration by Soluble CD100 and HSema III Semaphorins," *Tissue Antigens*, 2000, p. 103, vol. 55(Suppl. 1).
Giraudon, P., et al., "Semaphorin CD100 from Activated T Lymphocytes Induces Process Extension Collapse in Oligodendrocytes and Death of Immature Neural Cells,"Journal of Immunology, 2004, pp. 1246-1255, vol. 172(2).
Goldsby, R., et al., "Autoimmunity," *Kuby Immunology*, 4th ed., 2000, pp. 502-504, W.H. Freeman and Company, USA.
Herold, C., et al., "Activation Signals Are Delivered Through Two Distinct Epitopes of CD100, a Unque 150 kDa Human Lymphocyte Surface Structure Previously Defined by BB18 mAb,"*International Immunology*, 1995, pp. 1-8, vol. 7(1).
Kumanogoh, A., and H. Kikutani, "The CD100-CD72 Interaction: A Novel Mechanism of Immune Regulation," *Trends in Immunology*, 2001, pp. 670-676, vol. 22(12).

(Continued)

*Primary Examiner* — Chang-Yu Wang
(74) *Attorney, Agent, or Firm* — Alston & Bird LLP (57) ABSTRACT

The invention relates to the use a BD16 and/or BB18 anti-CD100 antibody or of a chimeric or humanized or human form thereof, or a fragment thereof, for the therapy or diagnosis of a central nervous system disorder, more particularly a myelin disorder or a disease that affects oligodendrocytes, such as multiple sclerosis or HTLV-1 associated myelopathy or peripheral myelinating cells.

4 Claims, 6 Drawing Sheets

OTHER PUBLICATIONS

Kumanogoh, A., et al., "Class IV Semaphorin Sema4A Enhances T-Cell Activation and Interacts with Tim-2," *Nature*, 2002, pp. 629-633, vol. 419(6907).

Kumanogoh, A., et al., "Requirement for the Lymphocyte Semsphorin, CD100, in the Induction of Antigen-Specific T Cells and the Maturation of Dendritic Cells,"*Journal of Immunology*, 2002, pp. 1175-1181, vol. 169(3).

Levin, M.C., et al., "Molecular Mimicry to Neurons Results in Neurological Disease,"*Society for Neuroscience Abstract Viewer and Itinerary Planner*, 2002, Abstract No. 415.3, vol. 2002.

Wang, X., et al., "Functional Soluble CD100/Sema4D Released from Activated Lymphocytes: Possible Role in Normal and Pathologic Immune Responses,"*Blood*, 2001, pp. 3498-3504, vol. 97(11).

Billard, C., et al., "Switch in the Protein Tyrosine Phosphatase Associated with Human CD100 Semaphorin at Terminal B-Cell Differentiation Stage," *Blood*, 2000, pp. 965-972, vol. 95(3).

Bougeret, C., et al., "Increased Surface Expression of a Newly Identified 150-kDa Dimer Early After Human T Lymphocyte Activation,"*The Journal of Immunology*, 1992, pp. 318-323, vol. 148(2).

Delaire, S., et al., "Biological Activity of Soluble CD100. II. Soluble CD100, Similarly to H-SemaIII, Inhibits Immune Cell Migration,"*The Journal of Immunology*, 2001, pp. 4348-4354, vol. 166.

Elhabazi, A., et al., "The Human Semphorin-Like Leukocyte Cell Surface Molecule CD100 Associates with a Serine Kinase Activity,"*The Journal of Biological Chemistry*, 1997, pp. 23515-23520, vol. 272(38).

Elhabazi, A., et al., "Structure and Function of the Immune Semaphorin CD100/SEMA4D,"*Critical Reviews™ in Immunology*, 2003, pp. 65-81, vol. 23(1&2).

Gauld, S., et al., "B Cell Antigen Receptor Signaling: Roles in Cell Development and Disease," *Science*, 2002, pp. 1641-1642, vol. 296.

Hall, K., et al., "Human CD100, A Novel Leukocyte Semaphorin ThatPromotes B-Cell Aggregation and Differentiation,"*Immunology*, 1996, pp. 11780-11785, vol. 93.

Herold, C., et al., "CD100 Defines a Newly Identified 150-kDa Human Lymphocyte Surface Structure," 1994, In Schlossman, S. et al., eds. *Leukocyte Typing V*, Section T, Oxford University Press, Oxford.

Ishida, I., et al., "Involvement of CD100, A Lymphocyte Semaphorin, in the Activation of the Human Immune System Via CD72: Implications for the Regulation of Immune and Inflammatory Responses," *International Immunology*, 2003, pp. 1027-1034, vol. 15(8).

Kumanogoh, A. and H. Kikutani, "Immune Semaphorins: A New Area of Semaphorin Research," *Journal of Cell Science*, 2003, pp. 3463-3470, vol. 116.

Shi, W., et al., "The Class IV Semaphorin CD100 Plays Nonredundant Roles in the Immune System: Defective B and T Cell Activation in CD100-Deficient Mice," *Immunity*, 2000, pp. 633-642, vol. 13.

Watanabe, C., et al., "Enhanced Immune Respones in Transgenic Mice Expressing a Truncated Form of the Lymphoctye Semaphorin CD100,"*The Journal of Immunology*, 2001, pp. 4321-4328, vol. 167.

Zhu, L., et al., "Semaphorin 4D (CD100) is Expressed on the Surface of Human Platelets and Proteolytically Shed During Platelet Activation," *Blood*, 2003, vol. 102(11).

Elhabazi, A., et al., "Biological Activity of Soluble CD100. I. The Extracellular Region of CD100 is Released from the Surface of T Lymphocytes by Regulated Proteolysis," *The Journal of Immunology*, 2001, pp. 4341-4347, vol. 166.

\* cited by examiner

USE OF ANTI-CD100 ANTIBODIES FOR THE TREATMENT OF INFLAMMATORY DISORDERS AFFECTING THE CENTRAL OR PERIPHERAL NERVOUS SYSTEM

The present invention relates to the use of anti-CD100 antibodies for the treatment or diagnosis of neuroinflammatory diseases.

CD100 is a human 150-kDa homodimer expressed at the surface of most hemopoietic cells, and its gene belongs to the Ig and semaphorin gene families (Bougeret et al, 1992; Herold et al, 1995). Semaphorin genes encode soluble and membrane-bound proteins, most of which have been shown to act as chemorepellents on growth cone guidance. Delaire et al., 1998, suggested that CD100 plays a role in T lymphocyte activation. Soluble CD100 was further shown to inhibit immune cell migration (Delaire et al., 2001). This human immune semaphorin CD100 (Hall et al., 1996; Bismuth et al., 2002) is released at high levels by T lymphocytes upon activation through proteolysis by a metalloproteinase (Elhabazi et al., 2001). It was further shown to be expressed in oligodendrocytes during myelination (Moreau-Fauvarque, 2002).

The inventors hypothesized that CD100 could play a critical role in neural-immune interactions in inflammatory situation.

Neuroinflammatory diseases, including multiple sclerosis (MS), the major inflammatory demyelinating disease of the CNS, and myelopathy associated with HTLV-I infection (HAM/TSP), are characterized by myelin destruction, oligodendrocyte and axonal loss in brain and spinal cord. Presence of activated T lymphocytes together with increased expression of inflammatory cytokines and metalloproteinases, correspond well with active lesions in the central nervous system (CNS) of patients. Infiltrating T lymphocytes are suspected to take part in cytotoxicity, inflammatory molecule synthesis, dysregulation of oligodendrocyte homeostasis and axonal damages.

The inventors investigated in vitro the effect of chronically activated T cells expressing sCD100, and recombinant sCD100, on human pluripotent neural precursors and on rat oligodendrocytes. These cellular contacts mimic interactions occurring during neuroinflammation between activated T lymphocytes and oligodendrocytes or pluripotent neural precursors still capable of generating neurons or oligodendrocytes in adult brain (Zhang et al., 1999).

The inventors have particularly analyzed cell survival and oligodendrocyte process extensions. They have shown that the specific anti-CD100 monoclonal antibodies called BD16 and BB18 were able to block the interaction of soluble CD100 with its receptor in activated T cells, whereby they prevented the apoptosis of oligodendrocytes in HTLV-1 associated disease.

The presence of sCD100 in the cerebrospinal fluid (CSF) and CD100-expressing activated T lymphocytes in post-mortem brains from HAM/TSP patients was also explored to support the functional relevance of the experimental results.

On that basis the inventors now propose to use the specific anti-CD100 antibodies, and especially the monoclonal antibodies called BD16 and BB18, in the treatment or diagnosis of neuroinflammatory diseases.

The treatment or diagnostic methods of the invention are useful for any subject or patient. "Treatment" refers to both therapeutic treatment and prophylactic or preventative measures. Those in need of treatment include those already with the disorder as well as those prone to have the disorder or those in which the disorder is to be prevented. The patient is preferably a human, preferably an adult, but the methods according to the present invention can also be applied to other mammals or vertebrates.

Anti-CD100 Monoclonal Antibodies

The preferred anti-CD100 antibodies used according to the present invention are monoclonal antibodies called BD16 and BB18.

BD16 is a mouse monoclonal antibody that is produced by a hybridoma deposited at the European Collection of Cell Cultures (ECACC), a Health Protection Agency Culture Collection (HPACC), Health Protection Agency, Centre for Emergency Preparedness and Response, Porton Down, Salisbury, Wiltshire SP4 0JG, United Kingdom on Jan. 7, 1992 (deposit number (92-01 0801), as described in the international patent application WO 93/14125. This deposit will be maintained under the terms of the Budapest Treaty on the International Recognition of the Deposit of Microorganisms for the Purposes of Patent Procedure. Access to this deposit will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the HPACC. The isolation of this antibody is described in Herold at al, 1995. This antibody can further be purchased from Beckman-Coulter. This antibody was tested on immune cell migration in Delaire et al., 2001.

BB18 is another mouse monoclonal antibody that is produced by a hybridoma deposited at the European Collection of Cell Cultures (ECACC), a Health Protection Agency Culture Collection (HPACC), Health Protection Agency, Centre for Emergency Preparedness and Response, Porton Down, Salisbury, Wiltshire SP4 0JG, United Kingdom on Jan. 7,1992 (deposit number 92-01 0802), as described in the international patent application WO 93/14125. This deposit will be maintained under the terms of the Budapest treaty on the International Recognition of the Deposit of Microorganisms for the Purpose of the Patent Procedure. Access to this deposit will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the HPACC. The isolation of this antibody is described in Boueret at al., 1992.

Both antibodies, which are Ig A, recognize the human form of the CD100 semaphorin, via conformational epitopes. Whereas BB18 induces internalization of CD100, BD16 promotes its release. Whereas BB18 maintains CD100 in association with kinases, BD16 dissociates these complexes. BD16 is co-mitogenic with CD2 and CD3, while BB18 is co-mitogenic with PMA (phorbol ester). In spite of these different characteristics and properties, both the BD16 and BB18 antibodies are useful as blocking antibodies.

Hybrid and recombinant forms of these antibodies, as well as fragments thereof (e.g., Fab, F(ab')$_2$ and Fv), are also useful according to the present invention, so long as they exhibit the desired biological activity.

This means that the antibodies or fragments thereof useful according to the invention are able to bind human CD100 with essentially the same affinity and specificity than the BD16 or BB18 antibody and, when used for purposes of prevention or treatment of a central nervous system or peripheral nervous system inflammatory disorder, exhibit essentially the same blocking property with regard to the activity of human CD100 than the BD16 or BB18 antibody.

Anti-CD100 Chimeric or Humanized Antibodies

Especially with regard to the therapeutics in humans, it may be advantageous to use chimeric or humanized forms of BD16 or BB18 antibodies.

Hybrid and recombinant antibodies may be produced by splicing a variable (including hypervariable) domain of an anti-CD100 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, so long as they exhibit the desired biological activity (See, e.g., Cabilly et al., U.S. Pat. No. 4,816,567; Mage and Lamoyi, in Monoclonal Antibody Production Techniques and Applications, pp. 79-97 (Marcel Dekker, Inc., New York, 1987)).

An aspect of the present invention encompasses using "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass.

"Humanized" forms of the BD16 or BB18 antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from mouse immunoglobulin. For the most part, humanized antibodies are human immunoglobulins (recipient antibody) in which residues from a complementarity-determining region (CDR) of the recipient are replaced by residues from a CDR of the non-human species (donor antibody) having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also comprises at least a portion of an immunoglobulin constant region (Fc), typically that of a human immunoglobulin (see Berger et al., 2002 for a review of the available techniques).

Full Human Anti-CD100 Antibodies

In another aspect of the invention one may use human anti-CD100 antibodies, i.e. human anti-CD 100 antibodies recognizing similar or closely related epitope(s) to BD16 or BB18. These antibodies are obtainable from a human immunoglobulin gene library.

Several methods for producing human antibodies are described e.g. in the International Patent Application WO 01/040306.

These methods include the phage display methods and nonhuman transgenic mice expressing genes of the human immune system. The methods typically work by immunizing a nonhuman transgenic animal having human immunoglobulin genes. The animal expresses a diverse range of human antibodies that bind to the antigen. Nucleic acids encoding the antibody chain components of such antibodies are then cloned from the animal into a display vector. Typically, separate populations of nucleic acids encoding heavy and light chain sequences are cloned, and the separate populations then recombined on insertion into the vector, such that any given copy of the vector receives a random combination of a heavy and light chains. The vector is designed to express antibody chains so that they can be assembled and displayed on the outersurface of a display package containing the vector. For example, antibody chains can be expressed as fusion proteins with a phage coat protein from the outersurface of the phage. Thereafter, display packages can be screened for display of antibodies binding to a target.

Useful cDNA libraries for human immunoglobulin heavy chain and light chain variable regions can also be built and expressed in a variety of different hosts, such as bacteria (e.g. E. coli) or viruses, such as a poxvirus (Smith et al, 2001) or a phage.

In the phage display methods, human immunoglobulin heavy chain and light chain variable regions may be cloned, combinatorially reasserted, expressed and displayed as antigen-binding human Fab or scfv ("single chain variable region") fragments on the surface of filamentous phage, especially phage M13, Fd and Fl. See Rader et al., (1997); Aujame et al., (1997); Hoogenboom, (1997); de Kruif et al., (1996); Barbas et al., (1996); Winter et al., (1994). The phage-displayed human antigen-binding fragments may then be screened for their ability to bind a chosen antigen.

Therapy

In a first aspect of the invention it is provided a method for the prevention or treatment of a central (CNS) or peripheral (PNS) nervous system inflammatory disorder, which method comprises administering an effective amount of BD16 and/or BB18 anti-CD100 antibody or of a chimeric or humanized form thereof, or a human form thereof, as well as fragments thereof to a patient in need of such treatment.

Another subject of the invention is the use of a BD16 and/or BB18 anti-CD100 antibody or of a chimeric or humanized form thereof, or a human form thereof, as well as fragments thereof, for the preparation of a medicament useful in the prevention or treatment of a central or peripheral nervous system inflammatory disorder.

Infiltration of the CNS or PNS by activated T lymphocytes can sustain the onset and progression of inflammatory diseases. The inventors herein point out the primary role of immune semaphorin in demyelination as soluble CD100, produced by virally-activated T lymphocytes, induced the apoptotic death of human neural precursors (with oligodendrocyte differentiating ability) and the progressive decrease in process extensions followed by death of immature oligodendrocytes. The specific expression of sCD100 in CSF of HAM/TSP patients and the presence of numerous infiltrating CD100/CD45R0-positive T lymphocytes in their spinal cord (in contrast with other neurological cases) substantiate the potential deleterious effect of CD100 in neuroinflammatory demyelinating diseases. The anti-CD100 antibodies may further be useful to prevent oligodendrocyte impairment or impairment of other peripheral myelinating cells, therefore extension of neurological disorders.

Accordingly the CNS or PNS inflammatory disorder the present invention is aimed at is preferably a myelin disorder or a disease that affects oligodendrocytes or other myelinating cells, e.g. peripheral myelinating cells. More particularly prevention or treatment of multiple sclerosis or HTLV-1 associated myelopathy is encompassed.

One can also cite more generally neuroinflammatory disorders, as well as oligodendrogliomas and leucodystrophies, Guillain-Barré syndrome, Alexander disease, Canavan disease, Krabbe disease, Pelizaeus-Merzbacher disease, Zellweger disease, Refsum disease, CACH disease, X-linked adrenoleucodystrophy, adrenoleucodystrophy, adrenomyeloneuropathy or leucodystrophies of undetermined origin, or polyradiculoneuritis as well as chronic polyradiculoneuritis.

In another aspect of the invention, the disorder is a post-trauma myelin disorder, as well as CNS or PNS lesions, for example caused by spinal cord injury or stroke.

Another subject of the invention is thus a method for stimulating axonal myelination, which method comprises administering to a patient in need of such treatment a therapeutically active amount of a BD16 and/or BB18 anti-CD100 antibody.

Pharmaceutical Compositions

Anti-CD100 antibodies can be formulated in pharmaceutical compositions, for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected, optionally directly into the central nervous system or in the brain, e.g. by intracerebroventricular injection for dispersion into other areas.

The suitable pharmaceutical compositions may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses of anti-CD100 antibodies used for the administration can be adapted as a function of various parameters, and in particular as a function of the mode of administration used, of the relevant pathology, or alternatively of the desired duration of treatment.

To prepare pharmaceutical compositions for antibody therapy, an effective amount of the protein may be dissolved or dispersed in a pharmaceutically acceptable carrier or aqueous medium.

Examples of pharmaceutical formulations are provided hereafter.

Pharmaceutical compositions comprise an effective amount of an anti-CD100 antibody in a pharmaceutically acceptable carrier or aqueous medium.

"Pharmaceutically" or "pharmaceutically acceptable" refer to molecular entities and compositions that do not produce an adverse, allergic or other untoward reaction when administered to an animal, or a human, as appropriate.

As used herein, a "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, intrathecal, intracerebroventricular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The anti-CD100 antibody may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; liposomal formulations time release capsules; and any other form currently used, including creams.

Other routes of administration are contemplated, including nasal solutions or sprays, aerosols or inhalants, or vaginal or rectal suppositories and pessaries.

In certain embodiments, the use of liposomes and/or nanoparticles is contemplated for the introduction of the antibodies. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs as a characteristic phase-transition temperature and results in an increase in permeability to ions, sugars and drugs.

Liposomes interact with cells via four different mechanisms: endocytosis by phagocytic cells of the reticuloendothelial system such as macrophages and neutrophils; adsorption to the cell surface, either by non-specific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membrane, or vice versa, without any association of the liposome contents. Varying the liposome formulation can alter which mechanism is operative, although more than one may operate at the same time.

Diagnosis

The inventors demonstrated the presence of sCD100 in the cerebrospinal fluid (CSF) and CD100-expressing activated T lymphocytes in post-mortem brains from HAM/TSP patients.

On that basis the present invention provides an in vitro method for diagnosis or determination of the evolution of a central nervous system (CNS) or peripheral nervous system (PNS) inflammatory disorder, which method comprises assaying a CD100 semaphorin in a biological sample of a test subject, compared with the level of a CD100 semaphorin in a biological sample of a control subject, wherein an increased level of CD100 is indicative of said disorder or of a poor prognosis, wherein the assay is an immunoassay employing a BD16 and/or BB18 anti-CD100 antibody, a chimeric or humanized form thereof, or a fragment thereof.

A "biological sample" is a fluid from a subject, including serum, plasma, blood, spinal fluid, cerebrospinal fluid, urine, ascites, pleural effusion, amniotic fluid, tears or saliva, or a tissue extract or a tissue or organ biopsy such as brain, spinal cord or nerves.

"A subject" or "a patient" is a vertebrate, e.g. a mammal, preferably a human being, regardless of his/her age, sex and general condition. Children and infants are also encompassed. The test subject may be asymptomatic, may be considered likely to develop the disease or condition. Subjects with a suspicion of myelin disorder or subjects who have already shown symptoms of the disease or condition can also be tested. Subjects who are predisposed to developing a CNS or PNS inflammatory disorder naturally are a preferred target.

The <<control subject>> may be a healthy subject or a subject without any myelin disorder. In order to determine the evolution of a CNS or PNS inflammatory disorder, it may be very useful to test a subject for the expression of CD100 or of a receptor thereof, and to monitor the effect of a drug or the spreading of the condition, by testing him/her a second time, e.g. a few weeks later. In that case the results of the second test are compared with the results of the first test, and in general also with the results obtained with a "healthy" subject. The "control subject" then refers either to the same test subject or to a "healthy subject".

"A CNS or PNS inflammatory disorder" includes any neuroinflammatory disorder, myelin disorder, or disease that affects oligodendrocytes, or other myelinating peripheral cells as described above. Diagnosis or monitoring of the evolution of multiple sclerosis or HTLV-1 associated myelopathy is more particularly contemplated. The in vitro method provided herein is particularly advantageous for that purpose, in that it makes it possible to easily and quickly assay the CD100 in a fluid sample, such as a CSF sample for instance.

In a preferred embodiment the invention provides an in vitro method for diagnosis or monitoring a HTLV-1 associated myelopathy in a patient, wherein the CD100 semaphorin is assayed in a CSF sample of the patient by means of an ELISA technique employing a BD16 and/or BB18 anti-CD100 antibody, a chimeric or humanized form thereof, or a human form thereof, as well as fragments thereof.

The term "diagnosis" refers to the determination or the confirmation of a disease or condition in a subject. The term "poor prognosis" means that the condition has worsened.

Methods for immunoassaying the CD100 semaphorin protein or a receptor thereof are well known by one skilled in the art. Such assays include competition, direct reaction, or sandwich type assays. Various techniques including Western blots, enzyme-labeled and mediated immunoassays, such as ELISAs; radioimmunoassays; immunoelectrophoresis; immunoprecipitation, etc., may be employed. ELISAs are preferred. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound CD100 in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (i.e. an anti-CD100 antibody) under suitable binding conditions such that the component is sufficiently immobilized to the support according to methods well known to those skilled in the art. After reacting the solid support with the solid phase component, any non-immobilized solid-phase components are removed from the support by washing, and the support-bound component is then contacted with a biological sample suspected of containing ligand moieties (i.e. CD100 molecules toward the immobilized antibodies) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with an anti-CD100 antibody. A biological sample containing or suspected of containing CD100 molecules is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample CD100 molecules, the plate washed and the presence of the secondary binding molecule detected using methods well known in the art.

Thus, in one particular embodiment, the presence of bound CD100 molecules from a biological sample can be readily detected using a secondary binder comprising another antibody, that can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antigenic polypeptides and antibodies specific for those proteins form complexes under precipitating conditions. In one particular embodiment, antibodies can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing CD100 molecules. The particle-antigen-antibody complexes aggregate and can be precipitated and separated from the sample using washing and/or centrifugation. The reaction mixture can be analyzed to determine the presence or absence of antibody-antigen complexes using any of a number of standard methods, such as those immunodiagnostic methods described above.

The above-described assay reagents, including the anti-CD100 antibodies, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The figures and examples illustrate the invention without restricting its scope.

LEGENDS OF FIGURES

FIG. 4: Involvement of CD100 in T cell-induced death in neural precursors and oligodendrocytes. This figure shows reduction of T cell-induced death in neural precursors (FIG. 4A) and oligodencrocyte by treatment with CD100-blocking antibody BD16. FIGS. 4B and 4C show that treatment with sCD100 recombinant protein mimicked the T cell-induced death of neural precursors (B) and oligodendrocytes (C) in a dose-dependent manner.

EXAMPLES

Example 1

Blockade of Neural Progenitor and Oligodendrocyte Apoptosis by BD16 Anti-CD100 Antibody in HTLV-1 Associated Myelopathy

Methods

To mimic a crosstalk between neural and immune cells, the inventors used an experimental paradigm consisting of transient cocultures of chronically activated T lymphocytes (HTLV-1 infected, no virus productive) with human multipotent neural precursors or rat primary oligodendrocytes. Such cell contact mimics interaction occurring in the brain between activated T cells and oligodendrocytes or multipotent neural progenitors capable of differentiating, in adult, into oligodendrocytes. The physiological relevance of the experimental data was examined by analyzing post mortem spinal cord and CSF from patients suffering neuroinflammatory disease, myelopathy associated with HTLV-1 myelopathy (HAM/TSP).

Model of T-Neural Cell Interaction: The human pluripotent neural precursor cell line Dev, has the ability to differentiate into neurons, astrocytes and oligodendrocytes (Derrington et al., 1998; Buzanska et al., 2001). Primary culture of rat glial cells (Szymocha et al., 2000) contained 35-54% oligodendrocytes, the remaining cells corresponding to glial acidic fibrillary protein (GFAP)-positive astrocytes. The oligodendrocytes (OL) comprised the distinct phenotypic stages of oligodendrocytes identified by a panel of cell specific antibodies (immunochemistry or flow cytometry, see below): pre-OL (OL precursor) expressing NG2 (10-15%), immature-OL expressing galactocerebroside (GalCer, 17-25%) and cyclic nucleotic phosphodiesterase (CNPase), mature-OL (premyelinating OL) expressing myelin associated glycoprotein (MAG, 3-15%) and myelin basic protein (MBP).

These neural cells were transiently co-cultured (Giraudon et al., 2000) with: 1—the human CD4+CD25+ no virus-productive T-cell line C8166/45 activated by HTLV-I infection (Popovic et al., 1983) which released soluble CD100 (sCD100) detected by ELISA (Hall et al., 1996) (1400 ng/ml); 2—the non activated CD4+ T cell line CEM. The T cells were eliminated by washing of neural culture and their elimination verified by the absence of CD4 antigen (flow cytometry). The neural cells were also treated with recombinant soluble CD100 (sCD100r) (0.6-10 ng/µl concentration) from transfected Jurkat cells (producing 800 ng/ml), used as such or purified on CD100 BB18-mAb column. Experiments were repeated three times.

Patients: The CNS tissue samples from 3 HAM/TSP patients and 2 non-infected patients (Parkinson disease, car crash) were examined for CD100-expressing T cells. Paraffin-embedded spinal cords were examined using routine (hematoxylin-eosin-safran) and Luxol Fast Blue for myelin detection. Spinal cord from these patients displayed moderate to marked atrophy in the thoracic level, thickening of the leptomeninges, perivascular infiltrates of immune cells, as previously described in Cartier et al., 1997. Degeneration of the lateral cortico-spinal and spinocerebellar tracts, diffuse loss of myelin and axons and astrocytosis were observed in the three cases. Characteristics of HAM/TSP Patients:

|  | Age/sex | Duration of illness | Cause of death | CNS neuropathology | | |
|---|---|---|---|---|---|---|
|  |  |  |  | inflam. | myelin/axonal loss | atrophy |
| case 1: | 62/F | 15 years | Pulmonary embolism | +++ | +++ | +++ |
| case 2: | 35/H | 4 years | Mesenteric thrombosis | ++ | +++ | ++ |
| case 3: | 65/F | 8 years | Pneumonia | + | + | + |

The CSF from patients suffering from TSP/HAM (9), meningitis (4) or encephalomyelitis (3) were examined for the presence of sCD100 by a sandwich ELISA as previously described in Delaire et al, 2001. All HAM/TSP patients tested were positive for HTLV-1 provirus.

Immunodetection: Astrocytes and oligodendrocytes were identified by immunofluorescence, in flow cytometry or on culture slide (Bougeret et al, 1992; Herold et al, 1995), with monoclonal antibodies (anti-CNPase, Sigma; anti-GalCer, anti-NG2, Chemicon Int.; anti-MAG, Boehringer Mannheim; anti-MBP, Serotec) or rabbit polyclonal antibody (anti-GFAP, Dako). Semaphorin receptors were detected with monoclonal anti-human plexin-B1 (N18-Tebu) and anti-MAM neuropilin-1 rabbit polyclonal antibody (Bagnard et al., 2001). T lymphocytes were detected in spinal cord sections from HAM/TSP patients by immunofluorescence with anti-CD45RO monoclonal antibody (clone UCHL1, Dako), and an anti-CD100 polyclonal antiserum, directed against the intracellular portion of the protein (AA799-813). After dewaxing with toluene and ethanol, sections were incubated in blocking solution (1% BSA, 0.3% triton, 1 h), then with specific antibodies (4° C./over night). Anti-mouse Alexa546 or anti-rabbit Alexa488 labeled antibodies (Molecular Probes) were then applied.

RNA Detection: mRNA were detected by extraction followed by reverse transcription and polymerase-chain reaction (RT-PCR) and Southern blotting using appropriate [$^{33}$P] dATP-5' end-labeled internal oligonucleotide probes, as previously described in Szymocha et al., 2000. Oligonucleotide primers were chosen from their mRNA sequences (GenBank access numbers HSU60800 for CD100, NM002663 for plexin-B1, NM012401 for plexin-B2, AF149019 for plexin-B3, L26081 for Sema-3A, NM01101 for β-actin, used as control). One set of oligomer was selected for amplification of a common 300 bp amplicon in the three plexin-B mRNA.

Apoptosis Analysis: In each experiment, apoptotic death was detected by the TUNEL (terminal deoxynucleotidyl transferase-mediated dUTP nick-end labeling)—method performed on culture slide (Promega), immunodetection of the executer caspase, active-caspase-3 (rabbit serum—Pharmingen) and detection of apoptotic bodies with Dapi (4',6-diamidino-2 phenylindol, Sigma, 1 µg/ml) staining of nucleus. Co-detection of TUNEL, active-caspase-3 and OL-markers was also performed.

Statistical Analysis: Total cells (Dapi staining), TUNEL and active-caspase-3-positive cells were counted in neural precursors and primary glial cells (15-20 microscope fields, 800-1000 cells, 3 experiments) using AnalySiS 3.2 software. Measure of oligodendrocyte process number and length was performed by using the same software. The values were expressed as mean±SEM. Difference between groups were calculated with the Student's t-test.

Results

Figure 1:
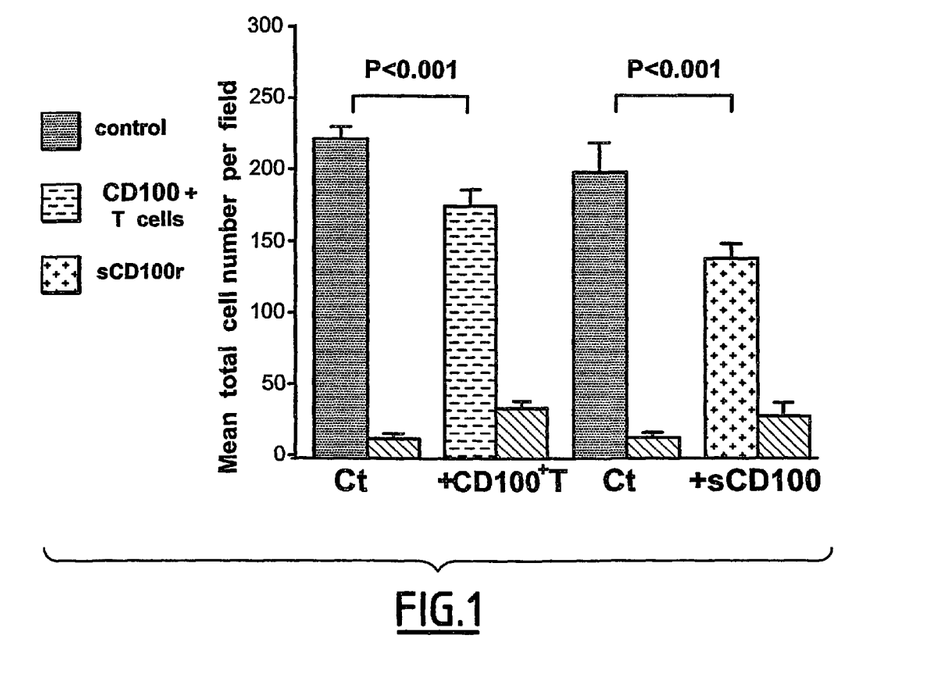
FIG. 1: CD100-induced death in human neural precursors. This figure shows apoptotic death in human neural precursors following transient contact with CD100-producing T lymphocytes (TUNEL positive cells) or treatment with soluble CD100 recombinant protein (active caspase-3 positive cells) (48 h post-treatment). Count (AnalySIS®) of total (non hatched bar) and active caspase-3 positive cells (hatched bar) is represented (mean±SEM, representative experiment).

The effect of soluble CD100 was investigated on human pluripotent neural precursors and rat primary oligodendrocytes by analyzing neural cell morphology and survival after contact with the chronically activated T cells producing high level of sCD100, C8166/45, or the non-activated and non-CD100-producing T cells, CEM. Apoptotic death of the human neural precursors was induced by C8166/45 T cells, as evidenced at 48 h post T cell-contact by the presence of apoptotic bodies in TUNEL positive cells and by detection, using immunofluorescence, of an enhanced number of active-caspase-3 positive cells (25.5±8.8 positive cells per field versus 11.3±3.7 in untreated cells) in three independent experiments (FIG. 1, a representative experiment). This corroborated the decrease in the total cell number (24±4.4% neural cell loss at 48 h post T cell contact and 58.5±9.2% at 72 h). CEM T cells had no effect on these neural precursors.

CD100-producing T cells also induced damages in rat primary glial culture. A progressive collapse and loss of process extensions were observed in GalCer-positive cells (immature-OL). The length and number of process extensions of these immature-OL were progressively reduced 24 h and 48 h post-contact (FIG. 2), as revealed in three independent experiments by the relative measure of their length (1.1±0.1 µm versus 2.7±0.2 µm in untreated glial culture at 48 h) and the count of processes (1.3±0.2 process per cell versus 4.3±0.5 in untreated glial culture at 48 h). In addition, an apoptotic death was observed at 48 h by the detection of TUNEL-positive cells and counting the active-caspase-3 positive cells (19.7±8.1 per field versus 7.3±5.5 in untreated cultures, 3 experiments). This resulted in the loss of a part of oligodendrocyte population, as shown by the reduced number of oligodendrocytes per field (FIG. 3—, a representative experiment) and the reduction in the percentage of total oligodendrocytes in the glial culture (26.8±3.6% loss at 48 h, 3 experiments). Interestingly, pre-OL (NG2-positive) and mature-OL (MBP-positive, FIG. 3-B) were not sensitive to T-cell induced apoptotic death in contrast with immature-OL (GalCer-positive). The number and morphology of astrocytes were unchanged. The CEM T cells had no effect on the neural precursors and glial culture.

Several lines of evidence indicated that sCD100 was involved in these T cell-induced damages. The anti-CD100 BD16 mAb was able to antagonize the T cell-induced effects on neural precursors and immature-OL when added in co-cultures. In fact, BD16-antibody dramatically decreased, in a dose-dependent manner, the number of apoptotic neural precursors at 48 h post-contact with T cells (FIG. 4-A) and reduced the cell loss (41.5±0.7% at 72 h versus 62±7.1% in antibody-untreated co-culture). Similarly, treatment of the rat co-culture with BD16-antibody reduced the number of TUNEL-positive cells and rescued immature-OL (CNPase-positive-cells). This resulted in a decrease in the T cell-induced oligodendrocyte loss (15.5±4.9% versus 26.3±5.4% in antibody-untreated co-culture).

Figure 2:
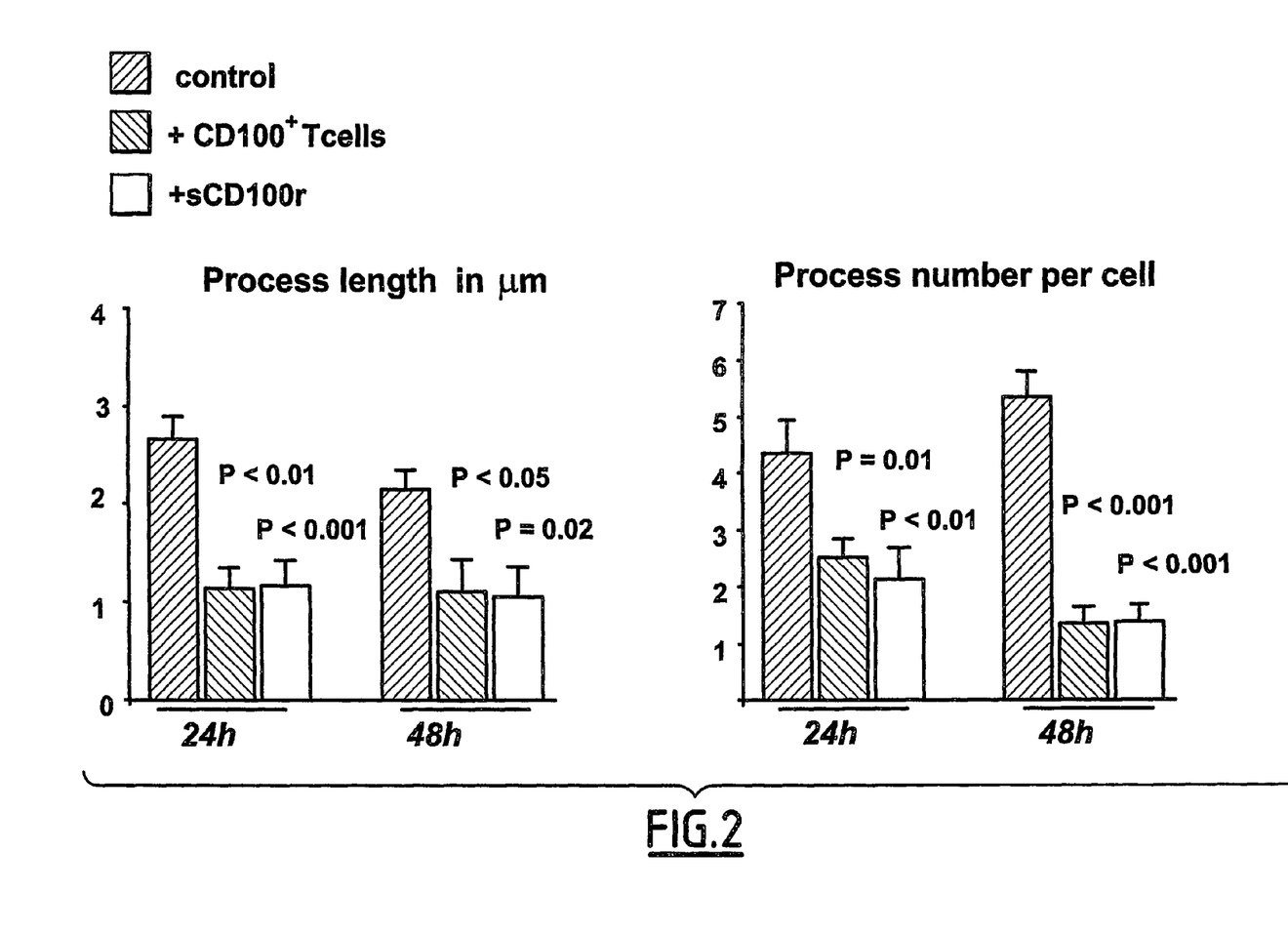
FIG. 2: CD100-induced alteration of oligodendrocyte process. This figure shows progressive loss of process extensions in immature rat oligodendrocytes (OL) following transient contact with CD100-producing T lymphocytes or treatment with soluble CD100 recombinant protein (24 h and 48 h post-treatment). The measure of OL process is represented following each treatment (mean±SEM, 10-20 measures, 3 experiments).
Figure 3:
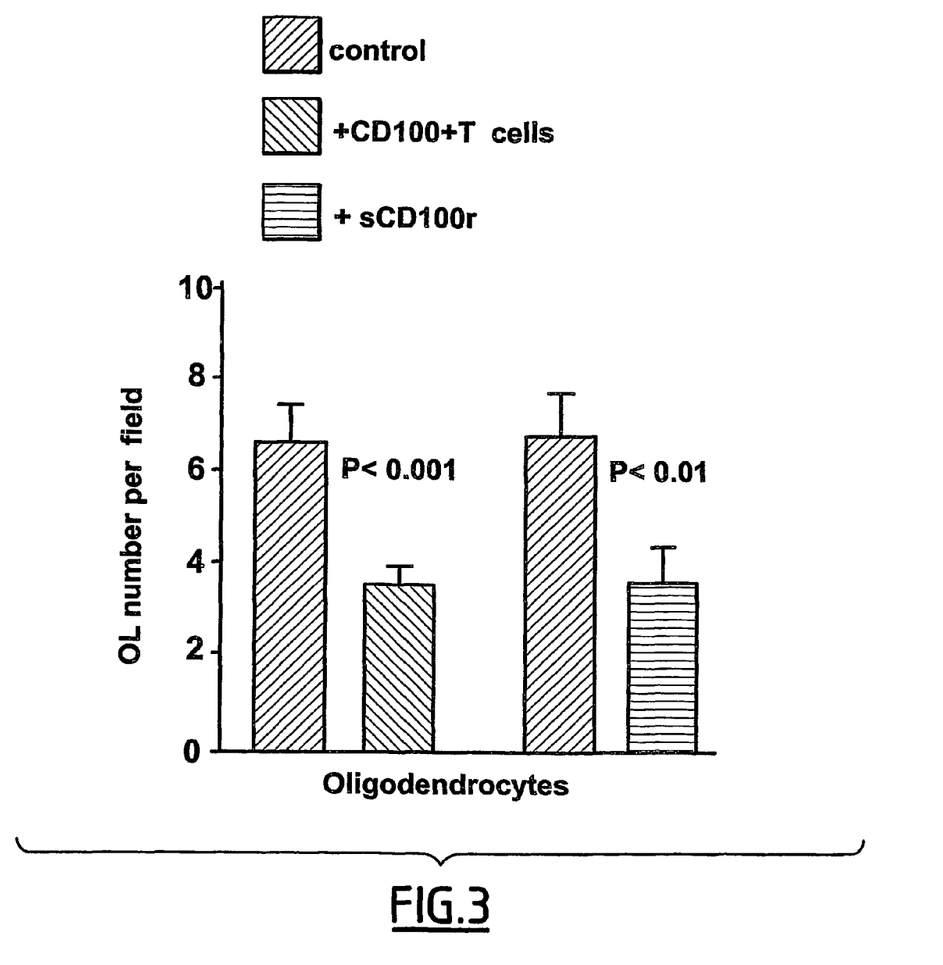
FIG. 3: CD100-induced death of immature-OL. This figure shows that transient contact with CD100-producing T lymphocytes or treatment with soluble CD100 recombinant induced loss of OL (48 h post-treatment). The total OL loss following each treatment is represented (mean±SEM OL per field, representative experiment).
Figure 4:
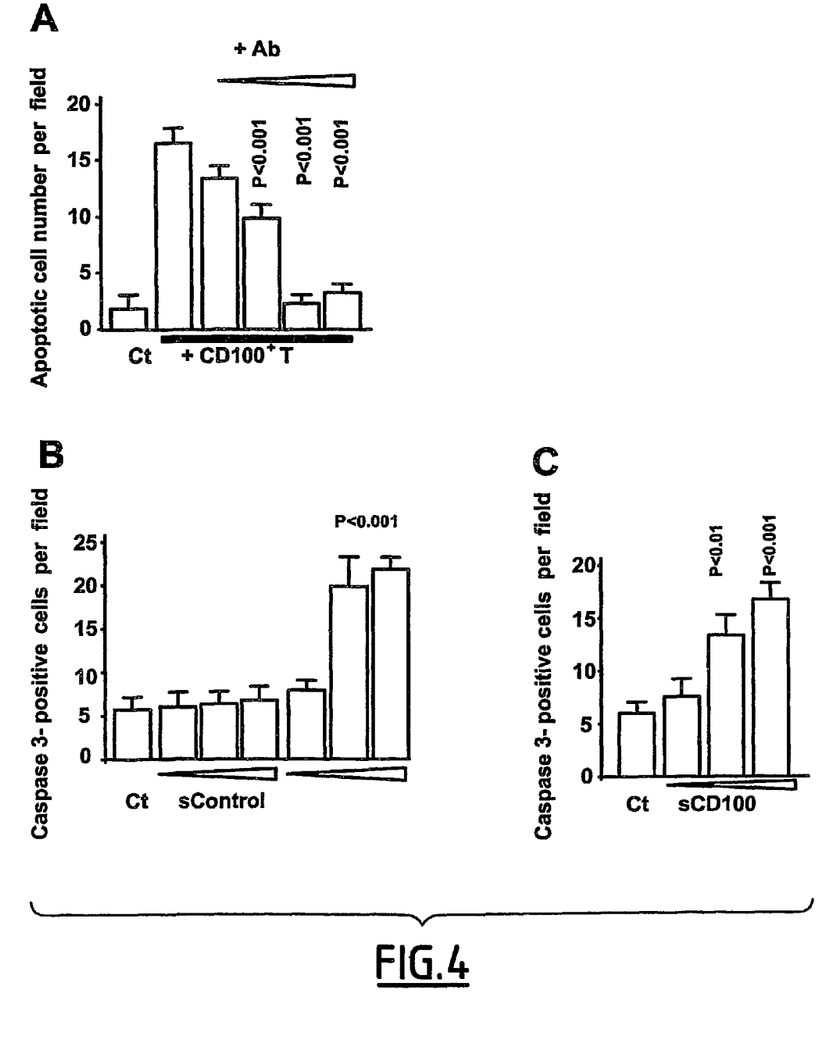

The direct effect of CD100 was demonstrated by treating the neural cells with recombinant sCD100 (sCD100r, 0.6-10 ng/µl, three experiments), released as a dimer from transfected Jurkat cells (Delaire et al., 2001). Similarly to contact with CD100-producing T cells, treatment with sCD100r induced apoptosis of neural precursors as demonstrated by the increased number of active-caspase-3 positive cells (25.3±3.6 per field in culture treated with 4.2 ng/µl sCD100r versus 11.1±2.3 in untreated culture) (FIG. 1—a representative experiment) and loss of these precursors (43.5±13.4% cell loss on 72 h). sCD100r induced apoptosis of neural precursors in a dose dependent manner as shown in FIG. 4-B. Treatment of glial primary culture with sCD100r (three experiments) also resulted in oligodendrocyte damage and apoptosis (FIGS. 2, 3, 4). A decrease in process number (1.4±0.2 process per oligodendrocyte at 48 h versus 5.3±0.4 in untreated culture) and their relative length (1±0.2 µm at 48 h versus 2.1±0.3 µm in untreated culture) were detected in immature-OL (GalCer-positive, FIG. 2). This was followed by an increased number of oligodendrocytes expressing active-caspase-3 (15±2.3 positive cells per field in culture treated with 4.2 ng/µl sCD100r versus 6±1.9 positive cells in untreated culture). In fact, sCD100r reduced the number of oligodendrocytes per field, as shown in FIG. 3 (one representative experiment), and the number of total oligodendrocytes (29±4% loss at 48 h post-treatment). Higher dose of sCD100r (10 pg/µl) induced the death of 37% total oligodendrocytes and 64% neural precursors at 72 h. Double-labeling (TUNEL and OL-markers) indicated that the immature-OL were sensitive to sCD100r similarly to CD100-producing T cells. The inventors also observed that SCD100r induced apoptosis of oligodendrocytes in a dose dependent manner (FIG. 4-C). In contrast, no detectable change was observed in astrocytes. The treatment of these human and rat neural cells with a supernatant from Jurkat permanently transfected with an unrelated molecule, CD27 (sControl), did not induce any change.

Figure 5:
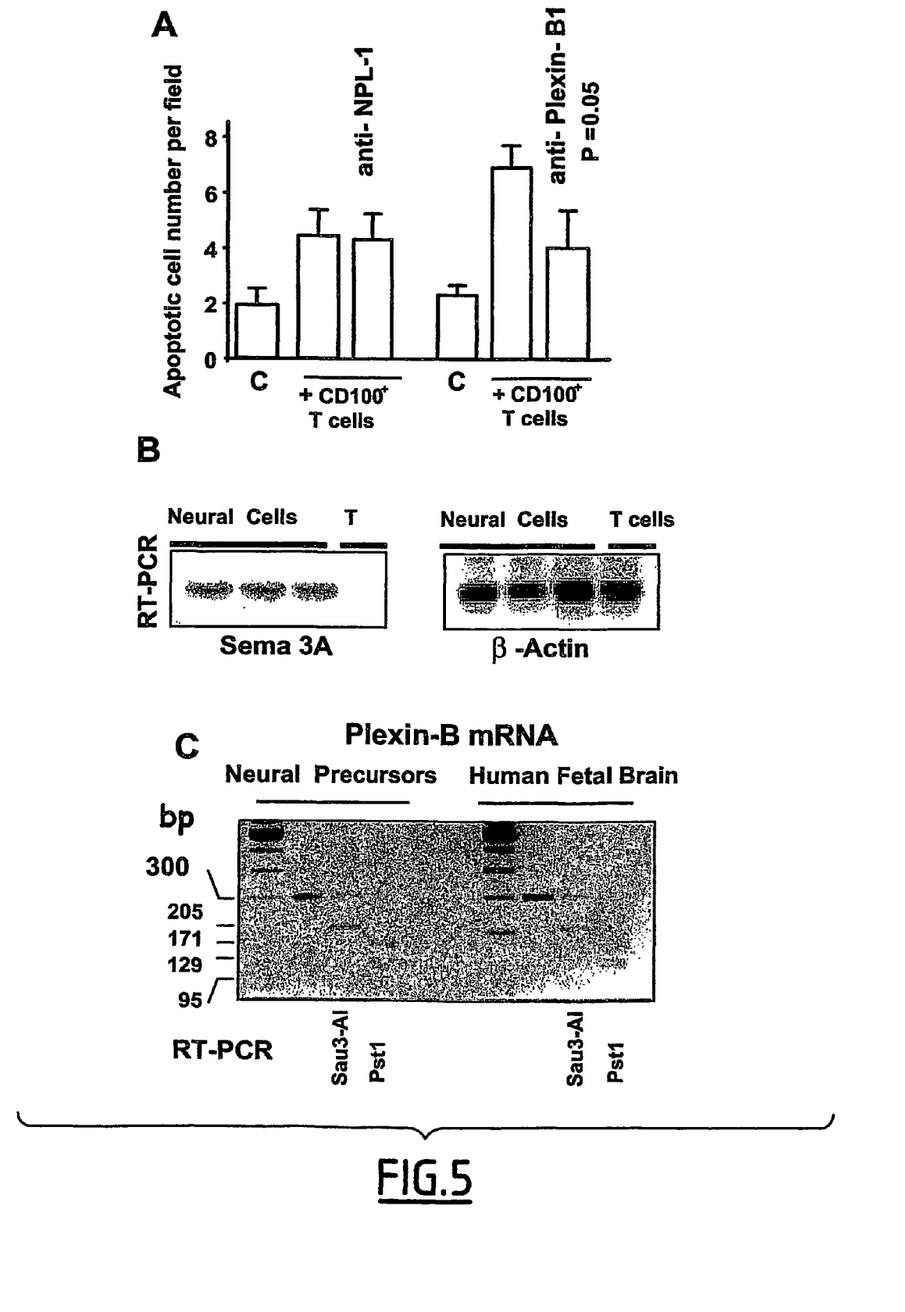
FIG. 5: Involvement of plexin-B in T cell-induced death of neural precursors A-Reduction of neural cell death by anti-plexin-B1 antibody; no effect of anti-neuropilin1 antibody (count of active caspase-3 positive cells: mean±SEM per field). B-Detection, by RT-PCR, of Sema3A mRNA in neural cells but not in T cells. C-Detection by RT-PCR and restriction enzyme digestion of plexin B family mRNA in human neural cells: Pst1 and Sau-3AI generated 171 pb and 129 bp, or 205 bp and 95 bp products, respectively from the 300 bp product common to Plexin-B1, plexin-B2 and plexin-B3 gene .D-Plexin-B1 immunodetected (FACS analysis) on human neural precursors.

CD100 could mediate its effect through receptors of neuropilin and plexin families present on immune and neural cells. Neuropilins act as co-receptors with plexins, while plexins alone behave as fully functional signal transducers for both transmembrane and secreted forms of semaphorins (Tamagnone et al., 1999). As neuropilin-1 is present on human neural precursors and mediates Sema 3A-induced apoptosis of these cells (Bagnard et al., 2001), neuropilin-1 and Sema 3A could be suspected in the T cell-induced apoptosis of neural precursors. However, when added in the T-neural cells co-culture, anti-MAM neuropilin-1 antibody (anti-NPL-1), shown to block the Sema 3A-induced neural precursors death (Bagnard et al., 2001), had no significant effect on the rate of death induced by CD100-producing T cells (FIG. 5-A). In addition, the possibility of an effect of anti-CD100 antibody BD16 on Sema 3A activity (Delaire et al., 2001), was ruled out by the absence of Sema 3A expression in T cells (RT-PCR, FIG. 5-B). These observations excluded the implication of neuropilin-1/Sema 3A in the T cell-mediated death. Involvement of plexins, in particular plexin-B1 identified as a receptor for sCD100 (Derrington et al., 1998), was further investigated. Presence of mRNA coding plexin-B1, B2 or B3 in human neural precursors and human fetal cortex (used as positive control) was checked by RT-PCR. Taking into account the high homology of RNA sequence between these three plexins, oligomers were selected for their ability to amplify a common 300 bp amplicon in neural precursors and human fetal brain. Amplicons were further identified by restriction enzymes Pst1 and Sau-3AI which can generate 171 bp and 129 bp products in the plexin-B1 and plexin-B3 amplicons, and 205 bp and 95 bp products in the plexin-B1 and plexin-B2 amplicons, respectively. As shown in FIG. 5-C, Pst1 generated the expected products from 300 bp amplicon, demonstrating the presence, in human neural precursors, of plexin-B1 or -B3 mRNA and -B2 at a less extent, as shown in human fetal cortex. The presence of plexin-B1 at the cell membrane was confirmed by immunodetection on alive neural precursors and flow cytometry on 50-54% cells (FIG. 5-D). The anti-plexin-B1 antibody-treatment of neural precursors, throughout the co-culture, significantly reduced the number of apoptotic neural cells (FIG. 5-A) and cell loss (5% versus 25.4% in untreated co-culture, at 48 h), indicating its possible involvement in this CD100-producing T cell mediated-apoptosis. The absence of anti-plexin-B1 effect on T-mediated oligodendrocyte apoptosis (despite the expression of plexin-B1) could be due to the uncapacity of anti-human plexin-B1 to block rat plexin-B1 or to the involvement of another plexin receptor.

Thus, these observations demonstrated that sCD100 produced by activated T lymphocytes severely impair immature-OL and human neural precursors, identifying semaphorin as a molecule of T cell-neural cell crosstalk during inflammation. The functional relevance of these experimental data was investigated in patients suffering neuroinflammatory disease compared to patients with other neurological disease.

The inventors particularly studied HAM/TSP patients as sCD100 is highly released by T lymphocytes chronically infected with HTLV-1. Expression of sCD100, analyzed in the cerebrospinal fluid (CSF) from patients with HAM/TSP (n=9), meningitis (n=4) or encephalomyelitis (n=3) by ELISA, revealed the presence of sCD100 at a level of 97.7±23.1 µg/ml in HAM/TSP' CSF (Table 1).

TABLE 1

Soluble CD100 in the CSF from HAM/TSP patients detected by ELISA (Hall et al., 1996). Patients with other neurological diseases were negative for CD100 detection in CSF

| HAM/TSP patient n° | CD100 (ng/ml) |
|---|---|
| 1 | 132.6 ± 29.9 |
| 2 | 66.6 ± 14.2 |
| 3 | 158.3 ± 17.2 |
| 4 | 79.6 ± 36.3 |
| 5 | 123.9 ± 42.7 |
| 6 | 60 ± 9.9 |
| 7 | 62.9 ± 14.2 |
| 8 | 57.9 ± 16.3 |
| 9 | 75 ± 27.6 |

This was in sharp contrast with meningitis and encephalomyelitis' CSF where CD100 was undetectable. Interestingly, these sCD100 levels are comparable to that found in T cells activated with CD3 crosslinking (40 ng/ml). The T cells present in CSF of HAM/TSP patients which are chronically activated by the viral protein Tax (Moritoyo et al., 1999), and produce high level of MMP could be one source of sCD100 expression detectable in those patients and not in patient with non neuroinflammatory disease. In addition, CD100 positive infiltrating cells were detected in post-mortem CNS from three HAM/TSP patients. In these patients, the level of immune cell infiltration correlates the extent of myelin/axonal loss and spinal cord atrophy (see Materials section). Analysis of immune cells infiltrating the spinal cord of these patients, using anti-CD100 and anti-CD45RO, a marker of activated T cells, showed the co-expression of these molecules. The highest density of double-labeled T lymphocytes was found in meningia and around blood vessels. Double-labeled T lymphocytes were also observed in parenchyma both in grey and white matters. Interestingly, astrocytosis in the white matter and around blood vessels was revealed by GFAP immunostaining, and the inventors had detected the metalloproteinase MMP-9 within astrocytosis in one of these HAM/TSP patients in a previous work[22]. In contrast, there is few CD45RO-positive but all CD100-negative T lymphocytes in spinal cords from uninfected patients.

These results show that T lymphocytes producing sCD100 induced apoptosis of neural progenitors and immature oligodendrocytes after a progressive decrease of their process extensions. Blockade by specific antibody of sCD100 from activated T cells, demonstrated that this immune semaphorin has the ability to trigger oligodendrocyte process alteration, and neural cell apoptosis likely through receptor of the plexin family. The presence of sCD100 in the CSF and of CD100 expressing T lymphocytes infiltrating the spinal cord of HAM/TSP patients points out the potential deleterious effect of sCD100 in the CNS during inflammation.

Example 2

BB18 Induces Internalization of CD100

Because membrane CD100 (mCD100) is down regulated from the surface of resting T-cells by the addition of CD100 mAb BD16 or BB18 the inventors studied the fate of CD100 following its surface labeling with biotin.

Freshly isolated human PBMC were surface-labeled with biotin. Cells were then incubated with the indicated ascite mAb (1/100 final dilution) or with PMA (1 ng/ml). After 1 hour of incubation, cell supernatants were collected and supplemented with protease inhibitors, subjected to filtration to eliminate cell debris followed by immunoprecipitation with a mixture of BD16 and BB18 mAb. In parallel, cells were washed twice with ice-cold PBS and lysed in NP40-based lysis buffer plus protease inhibitors before immunoprecipitation with the BD16/BB18 mixture. The CD100 ipp were subjected to SDS-PAGE and western blot using the peroxidase-conjugated streptavidin detection method. Similar results were obtained with PBMC isolated from most of the individuals tested.

The inventors thereby detected a soluble form of CD100 (sCD100) from the culture supernatants of cells incubated with BD16, or with the phorbol ester PMA whereas the incubation of resting T-cells with BB 18 rather provoked the internalization of the molecule.

Example 3

Detection of sCD100 in Neuroinflammatory Diseases

The inventors further tested 45 serum and 22 plasma (harvested on EDTA) from normal individuals were assayed (ELISA) for the presence of soluble CD100. Whereas the level of sCD100 in plasma was undetectable in most of them (18/22), the inventors were able to measure the level of sCD100 in the serum with a mean of 121 nanogramme/ml and standard deviation of 26 ng/ml. This was performed in comparison with a standard sCD100 after purification of sCD100 from a transfected cell line, producing high levels od sCD100 that was purified on BB18 mAb affinity column.

Figure 6:
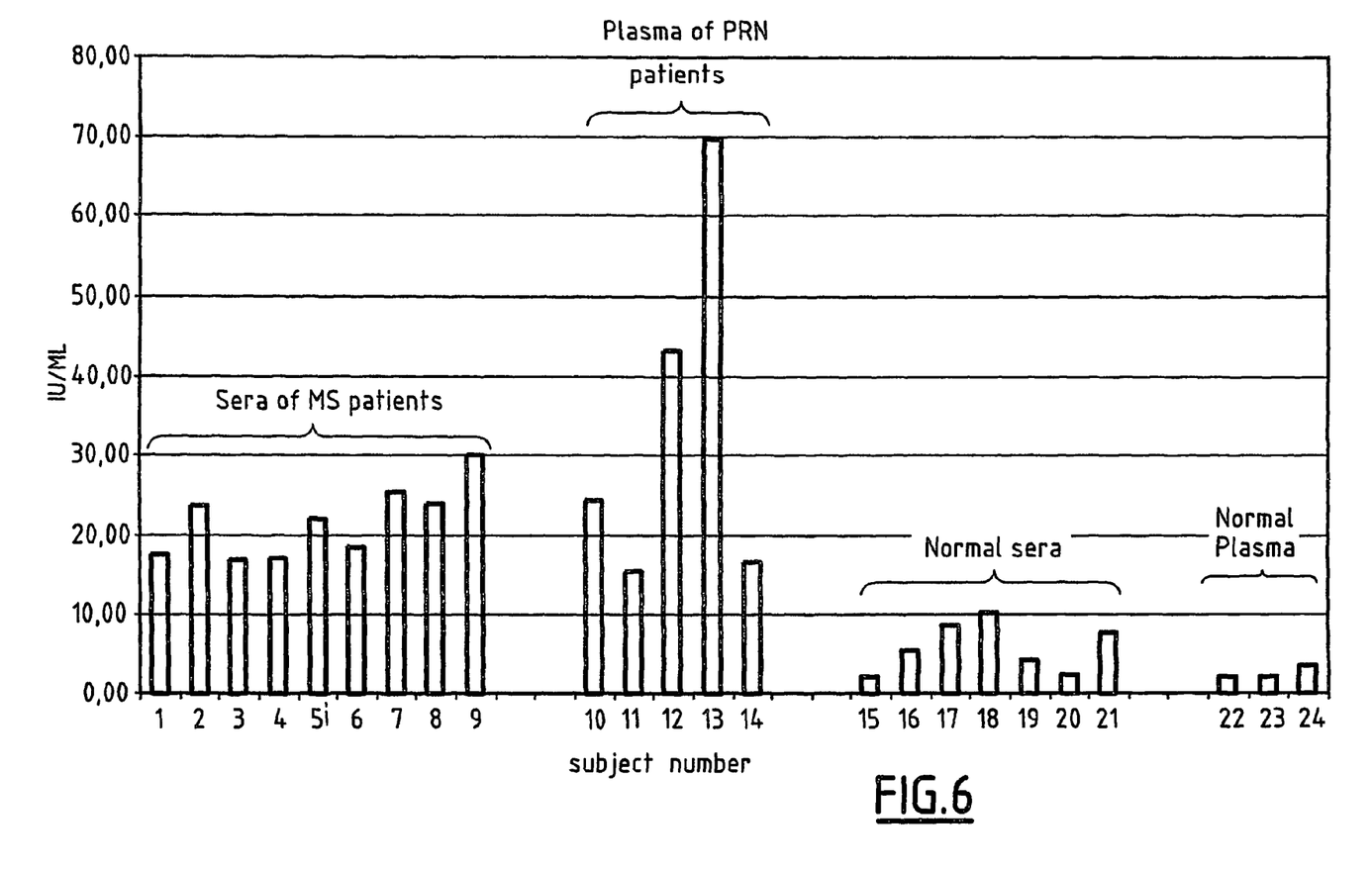
FIG. 6: Levels of sCD100 IU/ml in normal subjects or patients with neuroinflammatory diseases (MS=multiple sclerosis; PRN=polyradiculoneuritis).

The inventors next used a test with a different standard sCD100 (freeze-dried) giving the value of CD100 in International Unit (IU) per ml. Thus they could measure the levels of sCD100 in the sera of multiple sclerosis (MS) patients. The level of sCD100 in MS serum (21.66 IU/ml, SD 4.52) was at least twice the level observed in normal individuals (5.60 IU/ml, SD 3.55). In addition, the inventors tested the plasma of 5 patients with polyradiculoneuritis (PRN) in crisis. The level of sCD100 was even higher (33.84 IU/ml, SD 22.88) whereas the level of sCD100 in normals was unsignificant (1.91 IU/ml, SD 1.38). The results of these experiments are shown on FIG. 6.

These data confirm that sCD100 has a deleterious effect on the nervous system, particularly in neuro-inflammatory diseases involving myelinating cells such as HAM (HTLV1 associated myelopathy), MS and PRN.

These data further support the use of neutralizing anti-CD100 antibodies such as BD16 or BB18 monoclonal antibodies, to prevent or inhibit sCD100 effect.

The above ELISA method provides an easy way to monitor the evolution and crisis occurring MS or HAM for instance.

REFERENCES

Aujame et al., Human Antibodies 8:155-168 (1997)

Bagnard D, Vaillant C, Khuth S T, et al. Semaphorin 3A-vascular endothelial growth factor-165 balance mediates migration and apoptosis of neural progenitor cells by the recruitment of shared receptor. *J Neurosci* 2001; 21(10):3332-41.

Barbas et al., Trends in Biotechnol. 14:230-234 (1996)

Berger M, Vidya S, Abbas V, Therapeutic applications of monoclonal antibodies. *Am J Med Sci.,* 2002; 324(1):14-30

Bismuth G, Boumsell L. Controlling the immune system through semaphorins. *Sci STKE* 2002; 2002(128):RE4.

Bougeret C, Mansur I G, et al. Increased surface expression of a newly identified 150-kDa dimer early after human T lymphocyte activation. J. Immunol. 1992, 148(2):318-23

Buzanska L, Spassky N, Belin M F, et al. Human medulloblastoma cell line DEV is a potent tool to screen for factors influencing differentiation of neural stem cells. *J Neurosci Res* 2001; 65(1):17-23

Cartier L M, Cea J G, Vergara C, Araya F, Born P. Clinical and neuropathological study of six patients with spastic paraparesis associated with HTLV-I: an axomyelinic degeneration of the central nervous system. *J Neuropathol Exp Neurol* 1997; 56(4):403-13.

Delaire S, Elhabazi A, et al. CD100 is a leukocyte semaphorin, *Cell Mol. Life Sci.,* 1998; 54:1265

Delaire S, Billard C, Tordjman R, et al. Biological activity of soluble CD100. II. Soluble CD100, similarly to H-SemaIII, inhibits immune cell migration. *J Immunol* 2001; 166(7):4348-54

Derrington E A, Dufay N, Rudkin B B, Belin M F. Human primitive neuroectodermal tumour cells behave as multipotent neural precursors in response to FGF2. *Oncogene* 1998; 17(13):1663-72.

Elhabazi A, Delaire S, Bensussan A, Boumsell L, Bismuth G. Biological activity of soluble CD100. I. The extracellular region of CD100 is released from the surface of T lymphocytes by regulated proteolysis. *J Immunol* 2001; 166(7):4341-7

Giraudon P, Szymocha R, Buart S, et al. T lymphocytes activated by persistent viral infection differentially modify the expression of metalloproteinases and their endogenous inhibitors, TIMPs, in human astrocytes: relevance to HTLV-I-induced neurological disease. *J Immunol* 2000; 164(5):2718-27.

Hall K T, Boumsell L, Schultze J L, et al. Human CD100, a novel leukocyte semaphorin that promotes B-cell aggregation and differentiation. *Proc Natl Acad Sci USA* 1996; 93(21):11780-5

Herold C, et al, Activation signals are delivered through two distinct epitopes of CD100, a unique 150 kDa human lymphocyte surface structure previously defined by BB18mAb, Int Immunol, 1995, 7(1):1-8

Hoogenboom, Trends in Biotechnol. 15:62-70 (1997)

de Kruif et al., 17:453-455 (1996)

Moreau-Fauvarque C, CD100/Sema4D is expressed in oligodendrocytes during myelination, abstract submitted at the EMBO-FMI conference "Organizing the brain: genes, neurons, and circuits", February 2002.

Moritoyo T, Izumo S, Moritoyo H, et al. Detection of human T-lymphotropic virus type I p40tax protein in cerebrospinal fluid cells from patients with human T-lymphotropic virus type I-associated myelopathy/tropical spastic paraparesis. *J Neurovirol* 1999; 5(3):241-8

Ostberg et al. (1983), Hybridoma 2:361-367

Popovic M, Lange-Wantzin G, Sarin P S, Mann D, Gallo R C. Transformation of human umbilical cord blood T cells by human T-cell leukemia/lymphoma virus. *Proc Natl Acad Sci USA* 1983; 80(17):5402-6.

Rader et al., Current Opinion in Biotechnology 8:503-508 (1997)

Smith et al, Nature Medecine, 2001, 7:967-972

Szymocha R, Akaoka H, Dutuit M, et al. Human T-cell lymphotropic virus type 1-infected T lymphocytes impair catabolism and uptake of glutamate by astrocytes via Tax-1 and tumor necrosis factor alpha. *J Virol* 2000; 74(14):6433-41

Tamagnone L, Artigiani S, Chen H, et al. Plexins are a large family of receptors for transmembrane, secreted, and GPI-anchored semaphorins in vertebrates. *Cell* 1999; 99(1):71-80.

Winter et al., Ann. Rev. Immunol. 433-455 (1994)

Zhang S C, Ge B, Duncan I D. Adult brain retains the potential to generate oligodendroglial progenitors with extensive myelination capacity. *Proc Natl Acad Sci USA* 1999; 96(7):4089-94

The invention claimed is:

1. A method for treating multiple sclerosis in a subject, wherein said subject has a high level of soluble CD100 in a biological sample taken from said subject when compared to a control subject, said method comprising administering an effective amount of an anti-CD100 antibody to said subject, wherein said anti-CD100 antibody is selected from the group consisting of:

a) a BD16 anti-CD100 antibody;
b) a chimeric form of a BD16 anti-CD100 antibody;
c) a humanized form of a BD16 anti-CD100 antibody; and
d) an antigen-binding fragment of any one of a)-c).

2. The method of claim 1, wherein said antibody is a BD16 anti-CD100 antibody.

3. The method of claim 1, wherein said antibody is a chimeric form of a BD16 anti-CD100 antibody.

4. The method of claim 1, wherein said antibody is a humanized form of a BD16 anti-CD100 antibody.

* * * * *

UNITED STATES PATENT AND TRADEMARK OFFICE
CERTIFICATE OF CORRECTION

PATENT NO. : 8,067,247 B2  
APPLICATION NO. : 10/544031  
DATED : November 29, 2011  
INVENTOR(S) : Belin et al.

Page 1 of 1

It is certified that error appears in the above-identified patent and that said Letters Patent is hereby corrected as shown below:

In the title:

The title should read as follows:

--(54) USE OF ANTI-CD100 ANTIBODIES IN MULTIPLE SCLEROSIS--

Signed and Sealed this  
Seventeenth Day of July, 2012

David J. Kappos  
*Director of the United States Patent and Trademark Office*

UNITED STATES PATENT AND TRADEMARK OFFICE
CERTIFICATE OF CORRECTION

PATENT NO. : 8,067,247 B2
APPLICATION NO. : 10/544031
DATED : November 29, 2011
INVENTOR(S) : Belin et al.

It is certified that error appears in the above-identified patent and that said Letters Patent is hereby corrected as shown below:

Title Page, Item (54) and at Column 1, lines 1-4,

The title should read as follows:

--USE OF ANTI-CD100 ANTIBODIES IN MULTIPLE SCLEROSIS--

This certificate supersedes the Certificate of Correction issued July 17, 2012.

Signed and Sealed this
Fourteenth Day of August, 2012

David J. Kappos
*Director of the United States Patent and Trademark Office*